United States Patent [19]

Wester et al.

[11] Patent Number: 4,855,289

[45] Date of Patent: Aug. 8, 1989

[54] COMBINATION OF TWO ACTIVE SUBSTANCES

[76] Inventors: Per O. Wester, Kvarnvägen 1 E, 902 49 Umeå; Thomas R. Dyckner, Norevägen 7, 133 00 Saltsjöbaden, both of Sweden

[21] Appl. No.: 80,150

[22] Filed: Jul. 30, 1987

Related U.S. Application Data

[63] Continuation of Ser. No. 617,050, Jun. 4, 1984, abandoned.

[51] Int. Cl.[4] ..................... A61K 31/19; A61K 31/41; A61K 31/56; A61K 31/415
[52] U.S. Cl. .................................. 514/171; 514/155; 514/249; 514/255; 514/259; 514/326; 514/363; 514/391; 514/404; 514/425; 514/561; 514/568; 514/569; 514/571; 514/602; 514/604; 514/223.5
[58] Field of Search ............... 514/561, 171, 155, 225, 514/249, 259, 326, 363, 391, 404, 568, 569, 571, 602, 604, 255, 425

[56] References Cited

U.S. PATENT DOCUMENTS 4,137,326  1/1979  Fischer et al. ...................... 424/319

FOREIGN PATENT DOCUMENTS 1809119  6/1970  Fed. Rep. of Germany ...... 424/319

OTHER PUBLICATIONS

Physicians' Desk Reference 31st Ed., Medical Economics Co., Publisher (Oradell, N.J.) pp. 1090–1091 (1977).
Classen et al, "Experimental Studies on the Intestinal Absorption of Magnesium and Its Protective Effects Against Cardiac Hypertrophy and Nonocclusive Necroses", *Magnesium in Health and Disease,* SP Medical & Scientific Books, Publisher, pp. 521–535 (1980).
Chadda et al, "Magnesium and Cardiac Arrhythmia in Patients with Acute Infarction–Preliminary Observations", *Magnesium in Health and Disease,* SP Medical & Scientific Books, Publisher, pp. 545–549 (1980).
Shanker et al, "Effects of Furosemide on Serum and Urinary Magnesium in Congestive Heart Failure", *Magnesium in Health and Disease,* SP Medical & Scientific Books, Publisher, pp. 597–604 (1980).

*Primary Examiner*—Allen J. Robinson
*Attorney, Agent, or Firm*—JoAnn Villamizar; Irving M. Fishman

[57] ABSTRACT

The invention concerns the use of a compound with diuretic properties and of a magnesium supplementation in the form of magnesium monoaspartate hydrochloride, magnesium oxide, magnesium hydroxide or magnesium carbonate, and optionally of a potassium supplementation, and pharmaceutical preparations comprising a compound with diuretic properties and a magnesium supplementation in the form of magnesium monoasparate hydrochloride, magnesium oxide, magnesium hydroxide, or magnesium carbonate and optionally a potassium supplementation.

9 Claims, No Drawings

COMBINATION OF TWO ACTIVE SUBSTANCES

This application is a continuation of application Ser. No. 617,050 filed June 4, 1984, now abandoned.

The invention concerns the use of a compound with diuretic properties and of a magnesium supplementation in the form of magnesium monoaspartate hydrochloride, magnesium oxide, magnesium hydroxide or magnesium carbonate, and optionally of a potassium supplementation, and pharmaceutical preparations comprising a compound with diuretic properties and a magnesium supplementation in the form of magnesium monoaspartate hydrochloride, magnesium oxide, magnesium hydroxide, or magnesium carbonate and optionally a potassium supplementation.

It has been found, that the long-term treatment of patients with hypertension and/or congestive heart failure with compounds having diuretic properties, particularly of the 1,2,4-benzothiadiazine-1,1-dioxide-type, may give rise to potassium and magnesium deficiencies, accompanied by an increased cellular sodium content, which in turn may result in an increased cellular calcium content. In a recent study on patients with mild to moderate hypertension, potassium supplementation without changes in salt, particularly sodium chloride intake resulted in a mean reduction in blood pressure (systolic/diastolic) by 6/4 mm Hg (MacGregor et al., Lancet, Vol. 1982, p. 567.).

Surprisingly it has now been found, that in the long-term treatment of patients with hypertension or congestive heart failure, a magnesium supplementation in the form of the magnesium monoaspartate hydrochloride, causes a significant lowering of the blood pressure as compared with the control groups not receiving the magnesium supplementation. The mean value of the blood pressure lowering effect caused by the magnesium supplementation has been found to be 12/8 mm Hg. A similar effect on blood pressure has also been observed in patients with hypertension or congestive heart failure with magnesium supplementation in the form of magnesium oxide, magnesium hydroxide and magnesium carbonate.

Thus, through the combined administration of a compound with diuretic properties and the particular magnesium supplementation, and optionally of a potassium supplementation, the probability of therapeutic success can be substantially increased, since the effect of the two or optionally three types of active ingredients supplement each other in a surprising and unexpected manner.

The invention, therefore, concerns a new method of treating hypertension and/or congestive heart failure by using a compound having diuretic properties, magnesium monoaspartate hydrochloride, magnesium oxide, magnesium hydroxide or magnesium carbonate as a magnesium supplementation and optionally a potassium salt as a potassium supplementation, as well as new antihypertensive preparations comprising of a combination of a compound having diuretic properties, a magnesium compound selected from the group consisting of magnesium monoaspartate hydrochloride, magnesium oxide, magnesium hydroxide and magnesium carbonate, and optionally a potassium salt.

In order to determine the effects of the magnesium supplementation, particularly in the form of magnesium monoaspartate hydrochloride, on the blood pressure in patients receiving long term treatment for hypertension or congestive heart failure, or both, with compounds having diuretic effects, tests have been carried out according to the methods described below:

A total of 39 ambulatory patients, receiving long term treatment with diuretics for hypertension or congestive heart failure, or both, who had been receiving such treatment for over one year, were assigned to the test. Twenty patients (16 women and 4 men; mean age $62.2 \pm 4.2$ years) were randomised to receive treatment with magnesium monoaspartate hydrochloride. Eighteen of these patients had hypertension (six World Health Organisation grade I, 12 grade II) and four had congestive heart failure (two New York Heart Association grade II). Two of the four latter patients had both, hypertension and congestive heart failure (World Health Association grade II and New York Heart Association grade II, respectively, in both cases). The duration of hypertension was between 2 and 30 years (mean $9.7 \pm 6.8$ years), and the duration of diuretic treatment ranged from 1.5 years to 25 years (mean $8.3 \pm 5.5$ years). Thirteen of the hypertensive patients were receiving bendroflumethiazide (2.5 mg/day), four hydrochlorothiazide (12.5 mg/day), and one mefruside (25 mg/day). The patients with congestive heart failure alone were receiving bendroflumethiazide (2.6 mg/day; one patient) and furosemide (frusemide) (40 mg/day; one patient). The two patients with both, hypertension and congestive heart failure, were receiving bendroflumethiazide (40 mg/day) and furosemide (40 mg twice daily). All patients received additional potassium supplementation in the form of potassium chloride. None of the patients was receiving treatment with other agents known to influence the metabolism of magnesium. On administration to the test, the patients were seen twice at an interval of two to three days. Blood pressure and heart rate were recorded with the patient supine after 30 minutes rest and in the standing position. The blood pressure recordings were obtained with an ordinary sphygmomanometer, and diastolic pressure was recorded at the disappearance of the Korotkoff sound. The blood pressure obtained at the second initial visit was used in the protocol.

The patients continued their diuretic treatment, but received supplementation with magnesium monoaspartate hydrochloride (15 mmol/day, i.e. 365 mg magnesium or 3689 mg magnesium monoaspartate hydrochloride/day). After one month, the blood pressure was taken as on admission. After six months of treatment the procedure carried out on admission was repeated.

The patients randomised to form the control group consisted of 10 women and 9 men (mean age $67.8 \pm 4$ years). Seventeen patients had hypertension (2 World Health Organisation grade 1, 15 grade II) and 5 had congestive heart failure (4 New York Heart Association grade II, 1 grade III). Three of the patients had both, hypertension (World Health Organisation grade II) and congestive heart failure (2 grade II, 1 grade I). The duration of the diuretic treatment ranged from 1 to 20 years (mean $6.1 \pm 4.5$ years). Eight patients were receiving bendroflumethiazide (2.5 mg/day), 3 hydrochlorothiazide (12.5–25 mg/day), 3 chlorthalidone (25–50 mg/day), and 5 furosemide (40–80 mg/day). All patients received potassium supplements in the form of potassium chloride, and none was taking any treatment known to influence the metabolism of magnesium. Sampling procedures were the same as for the treatment group. The control group patients continued their treatment unchanged throughout the test.

In the treatment group, 19 of the 20 patients showed a significant decrease in blood pressure. In 3 patients, the dosage of the magnesium monoaspartate hydrochloride had to be reduced to 5–10 mmol/day (122–244 mg magnesium or 1230–2760 mg magnesium aspartate hydrochloride/day), because of too low blood pressure and resulting dizziness. In 3 other patients, the thiazide dosage was reduced for the same reasons as mentioned before. Despite these therapeutic changes, both supine and standing blood pressures had fallen significantly after six months treatment with the magnesium supplementation (mean supine blood pressure: 152±20/93±11 mm Hg before and 140±15/85±7 mm Hg after test (significance of difference: p<0.001); mean standing blood pressure: 145±17/93±13 mm Hg before and 139±18/87±10 mm Hg after test (significance of difference: p<0.05). There was no significant difference in the mean heart rate before (76±13 beats/min) and after (75±11 beats/min) treatment. In the control group, no significant differences were recorded in blood pressure before and after six months treatment (mean supine bood pressure 154±26/90±11 mm Hg before and 154±26/86±13 mm Hg after test; mean standing blood pressure 152±27/91±10 mm Hg before and 154±27/89±12 mm Hg after test).

Compounds with diuretic properties, useful in the method of treatment of hypertension and/or congestive heart failure according to the present invention, are substances which increase diuresis both through renal and extra-renal action on the tissue. It is possible to use substances possessing an inhibiting action on re-resorption in the tubulus, such as, for example, especially compounds having diuretic, as well as saluretic properties, as well as others, such as, for example, described and classified by Cragoe in "Diuretics" (Monograph in the series on Chemistry and Pharmacology of Drugs), published by John Wiley & Sons (1983).

Especially mentioned subclasses of diuretic compounds are benzothiadiazine derivatives, such as thiazides and hydrothiazides, benzenesulfonamides, phenoxyacetic acids, quinazolinesulfonamides, thiadiazolesulfonamides, such as 1,3,4-thiadiazolesulfonamides, pyrazolinone derivatives, thiazolidones, imidazolidinones and cycloamidines, as well as diuretic compounds having spiroxane-type steroid structures.

Particularly suitable thiazides are those of the formula I

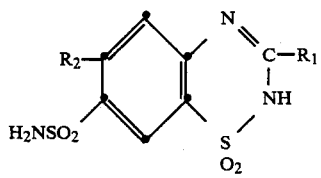

(I)

wherein $R_1$ is hydrogen or phenyl-lower alkylthio-lower alkyl, and $R_2$ is halogeno or trifluoromethyl, $R_1$ is phenyl-lower alkyl-thio-lower-alkyl, being especially a radical, wherein the lower alkyl portion has up to 4 C-atoms and especially 1 C-atom, and wherein the phenyl group may be substituted, e.g. by methyl, or is especially unsubstituted, such as benzyl-thio-methyl. A halogen atom is particularly fluorine and especially a chlorine atom.

Amongst those compounds embraced by formula I should be mentioned above all:

6-chloro-7-sulfamoyl-1,2,4-benzothiadiazine-1,1-dioxide (chlorothiazide), 6-trifluoromethyl-7-sulfamoyl-1,2,4-benzothiadiazine-1,1-dioxide (flumethiazide), and 3-benzylthiomethyl-6-chloro-7-sulfamoyl-1,2,4-benzothiadiazine-1,1-dioxide (benzthiazide).

Particularly suitable hydrothiazides are those of formula II

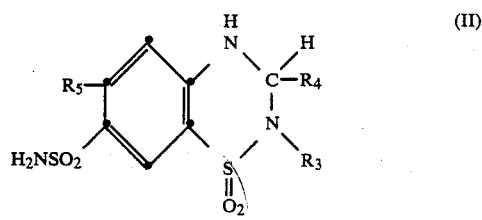

(II)

wherein $R_3$ is hydrogen or methyl, $R_4$ is hydrogen, lower alkyl with up to 4 carbon atoms, such as methyl, ethyl, n-propyl, isopropyl, n-butyl and isobutyl, allyl, cycloalkyl or cycloalkenyl with 5 to 8 ring members, such as cyclopentyl, cyclohexyl, cyclopentenyl, cyclohexenyl, or norbornenyl, cycloalkyl-lower alkyl, such as cyclopentylmethyl or cyclohexylmethyl, optionally substituted, especially halogeno-substituted, phenyl-lower alkyl, such as benzyl, 4-chloro-benzyl, 4-fluorobenzyl or 1- or 2- phenylethyl, halogeno-lower alkyl, such as chloromethyl, dichloromethyl, trichloromethyl or trifluoromethyl, optionally substituted lower alkylthio-, lower alkenylthio- or phenyl-loweralkylthio-lower alkyl, e.g. methylthiomethyl, methylthioethyl, trifluoroethylthiomethyl, allylthiomethyl or benzylthiomethyl, or 2,5-dioxopyrrolidin-1-yl-methyl (succinimidomethyl), and $R_5$ is halogeno, particularly chloro, or trifluoromethyl.

Amongst those hydrothiazides embraced by formula II should be mentioned above all:

6-chloro-7-sulfamoyl-3,4-dihydro-1,2,4-benzothiadiazine-1,1-dioxide (hydrochlorothiazide), 3-ethyl-6-chloro-7-sulfamoyl-3,4-dihydro-1,2,4-benzothiadiazine-1,1-dioxide (ethiazide), 3-trichloromethyl-6-chloro-7-sulfamoyl-3,4-dihydro-1,2,4-benzothiadiazine-1,1-dioxide (tetrachloromethiazide), 3-benzyl-6-trifluoromethyl-7-sulfamoyl-3,4-dihydro-1,2,4-benzothiadiazine-1,1-dioxide (bendroflumethiazide), 2-methyl-3-(2,2,2-trifluorethylthiomethyl)-6-chloro-7-sulfamoyl-3,4-dihydro-1,2,4-benzothiadiazine-1,1-dioxide (polythiazide), 3-(2,2,2-trifluoroethylthiomethyl)-6-chloro-7-sulfamoyl-3,4-dihydro-1,2,4-benzothiadiazine-1,1-dioxide (thiarene), 3-(5-norbornen-2-yl)-6-chloro-7-sulfamoyl-3,4-dihydro-1,2,4-benzothiadiazine-1,1-dioxide (cyclothiazide), 2-methyl-3-chloromethyl-6-chloro-7-sulfamoyl-3,4-dihydro-1,2,4-benzothiadiazine-1,1-dioxide (methyclothiazide), 3-dichloromethyl-6-chloro-7-sulfamoyl-3,4-dihydro-1,2,4-benzothiadiazine-1,1-dioxide (trichlormethiazide), 3-cyclopentylmethyl-6-chloro-7-sulfamoyl-3,4-dihydro-1,2,4-benzothiadiazine-1,1-dioxide (cyclopenthiazide), 6-trifluoromethyl-7-sulfamoyl-3,4-dihydro-1,2,4-benzothiadiazine-1,1-dioxide (hydroflumethiazide), 3-isobutyl-6-chloro-7-sulfamoyl-3,4-dihydro-1,2,4-benzothiadiazine (butizide),
3-n-butyl-6-trifluormethyl-7-sulfamoyl-3,4-dihydro-1,2,4-benzothiadiazine-1,1-dioxide (penfluthiazide),
3-(allylthiomethyl)-6-trifluoromethyl-7-sulfamoyl-3,4-dihydro-1,2,4-benzothiadiazine-1,1-dioxide (altizide) and
3-benzylthiomethyl-6-chloro-7-sulfamoyl-3,4-dihydro-1,2,4-benzothiadiazine-1,12-dioxide (benzthiazide).

Particularly suitable benzenesulfonamides are those of formula III

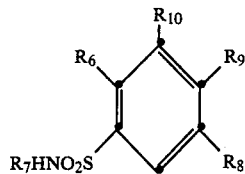

wherein $R_6$ is chloro, methyl, trifluoromethyl, phenoxy, or benzyl, $R_7$ is primarily hydrogen, as well as methyl, phenyl, 4-aminophenyl, 4-methoxyphenyl, or allyl, $R_8$ is carboxy, optionally substituted lower alkoxycarbonyl, such as ethoxycarbonyl or diethylaminoethoxycarbonyl, optionally substituted, particularly N-lower alkylated, carbamoyl, such as carbamoyl, N-methylcarbamoyl, N-ethylcarbamoyl, N,N-dimethylcarbamoyl, N,N-diethylcarbamoyl, dimethyl-aminocarbamoyl, diethylaminocarbamoyl, pyrrolidino-, piperidino- or 2,6-dimethylaminopiperidino-carbamoyl, lower alkyl-sulfonyl, such as methylsulfonyl, ethylsulfonyl, n-propylsulfonyl, or n-butylsulfonyl, optionally substituted sulfamoyl, e.g. sulfamoyl, N-methylsulfamoyl, N-ethylsulfamoyl, N-allylsulfamoyl, N-furfuryl- or N-tetrahydrofurfuryl-sulfamoyl, N-(2-methyltetrahydrofurfuryl)-sulfamoyl, N-(2-methyl-oxo-tetrahydrofurfuryl)-sulfamoyl, N-dimethylsulfamoyl, N,N-diethylsulfamoyl, piperidinosulfonyl, N-methyl-N-carboxymethylsulfamoyl, N-methyl-N-furfuryl-sulfamoyl, N-methyl-N-(2-methyl-4-oxo-tetrahydro-furfuryl)-sulfamoyl, 1-isoindolinyl, 3-hydroxy-1-oxo-isoindolin-3-yl, or tetrazolyl, or is bonded as carbamoyl radical to a lower alkyl group $R_9$ to form a 1-oxo-2-cyclphexyl-2-aza-1,3-propylene grouping, $R_9$ is hydrogen, lower alkyl, e.g. methyl or ethyl, or optionally substituted amino, such as amino, methylamino, ethylamino, benzylamino, furfurylamino, tetrahydrofurfurylamino, thenylamino, 4-sulfamoyl-benzyl-amino or 3-hydroxy-but-2-enylideneamino, and $R_{10}$ is hydrogen, chloro or optionally substituted amino, such as lower alkyl-amino, e.g. N-methylamino, N-ethylamino, N-n-propylamino, N-iso-propylamino, N-n-butylamino, N,N-dimethylamino, or N,N-diethylamino, as well as pyrrolidino.

Amongst those compounds of the formula III there should especially be mentioned:
2-chloro-5-[N-methyl-N-(2-methyl-5-oxo-tetrahydrofurfuryl)-sulfonamide]-benzenesulfonamide (oxomefruside),
4-chloro-6-methylbenzene-1,3-disulfonamide (disulfamide),
4-chloro-6-aminobenezen-1,3-disulfonamide (chloraminophenamide),
2-methyl-5-n-butylsulfonyl-benzene-sulfonamide,
4-chloro-benzene-1,3-disulfonamide (clofenamide),
3-sulfonamido-4-chloro-benz-amide (sulclamide),
2-chloro-4-[N-methyl-N-(2-methyl-tetrahydrofurfuryl)-sulfamoyl]-benzene sulfonamide (mefruside),
2-chloro-5-[3-hydroxy-1-oxo-isoindolin-3-yl]-benzenesulfonamide (chlorthalidone),
1-oxo-2-cyclohexyl-5-chloro-6-sulfamoyl-1,2-dihydroisoindole (dorexalone),
2-chloro-5-[N-(2-,6-dimethylpiperidino)-carbamoyl]-benzenesulfonamide (clopamide),
2-chloro-4-furfurylamino-5-carboxy-benzene-sulfonamide (furosemide),
2-chloro-4-benzylamino-5-carboxy-benzene-sulfonamide,
3-(n-butylamino)-4-phenoxy-5-sulfamoyl-benzoic acid (bumetanide),
4-chloro-2',6'-dimethyl-5-sulfamoylsalicyl-anilide (xipamide),
4-chloro-N-(2-methyl-1-idolinyl)-3-sulfamoylbenzamide (indapamide),
2-chloro-4-furfurylamino-5-(2-diethylamino-ethoxy)-carbonylbenzenesulfonamide (Nuriban ®)
5-allylsulfamoyl-2-chloro-4-(3-hydroxy-but-2-enylideneamino)-benzene-sulfonamide (ambuside),
2-chloro-5[-N-(2-methyl-tetrahydrofurfuryl)-sulfonamido]-benzenesulfonamide (normefruside),
4-chloro-3-(N-methyl-sulfonamido)-N-methylbenzamide (diapamide),
4,4-methylen bis[benzenesulfonamide] (Nirexon ®),
3-(pyrrolidin-1-yl)-4-phenoxy-5-sulfamoyl-benzoic acid (piretanide), and
3-(n-butylamino)-4-benzyl-5-sulfamoyl-benzoic acid (besumside).

Particularly suitable phenoxyacetic acids are those of formula IV

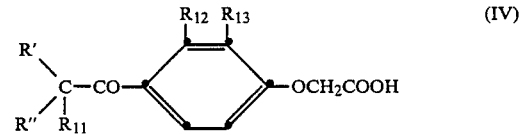

wherein R' is lower alkyl and R" is phenyl or R' and R" together are methylene, $R_{11}$ is lower alkyl or methylene which is fused to the ortho-position of the benzene nucleus to give an indanone ring, $R_{12}$ is halogeno or lower alkyl, and $R_{13}$ is hydrogen, halogeno or lower alkyl, or $R_{12}$ and $R_{13}$ together represent but-1,3-dienylene-(1.4).

A lower alkyl radical has especially 1 to 7, above all 1 to 4 C-atoms and preferably respresents an unbranched radical, such as n-propyl, n-butyl and especially methyl and ethyl. A halogen atom is bromo, iodo or fluoro and especially chloro.

As suitable compounds of above formula IV should especially be mentioned:
[2,3-dichloro-4-(2-methylene-butyryl)-phenoxy]-acetic acid (ethacrynic acid),
[(6,7-dichloro-2-methyl-1-oxo-2-phenyl-5-indanyl)-oxy]-acetic acid (indacrinone),
[2,3-dimethyl-4-(2-methylene-butyryl)-phenoxy]-acetic acid,
[2-methyl-3-chloro-4-(2-methylene-butyryl)-phenoxy]-acetic acid, and
[4-(-2-methylene-butyryl)-1-naphthoxy]-acetic acid.

Particularly suitable quinazoline sulfonamides are those of the formula V

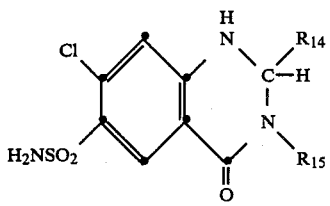

wherein R₁₄ is lower alkyl, such as methyl, ethyl, or n-propyl, or phenyl, and R₁₅ is hydrogen, phenyl or o-tolyl.

Suitable compounds of above formula V, which are of particular interest, are:
7-chloro-1,2,3,4-tetrahydro-2-methyl-4-oxo-3-o-tolyl-6-quinazolinesulfonamide (metolazone),
7-chloro-1,2,3,4-tetrahydro-2-phenyl-4-oxo-6-quinazolinesulfonamide (fenquizone), and
7-chloro-1,2,3,4-tetrahydro-2-ethyl-4-oxo-6-quinazolinsulfonamide (quinethazone).

Thiadiazolesulfonamides are especially 1,3,4-thiadiazolesulfonamides of formula VI

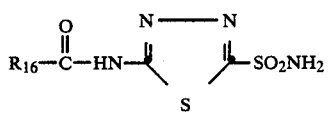

wherein R₁₆ is lower alkyl of at most 4 C-atoms, such as methyl, ethyl, n-propyl or n-butyl.

Of special interest as diureic compounds of the thiadiazolesulfonamide type are
5-acetamido-1,3,4-thiadiazole-2-sulfonamide (acetazolamide),
5-propionamido-1,3,4-thiadiazole-2-sulfonamide (propazolamide), and
5-butyramido-1,3,4-thiadiazole-2-sulfonamide (butazolmside).

Pyrazolinone derivatives are especially the 3-substituted 1-aralkyl-pyrazolin-5-ones of formula VII

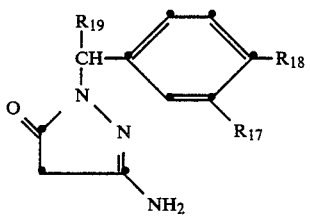

wherein R₁₇ and R₁₈ are hydrogen or chloro, and R₁₉ represents hydrogen and lower alkyl of at most 4-C-atoms, such as methyl, ethyl, n-propyl, isopropyl and n-butyl.

Of particular interest is in this group of diuretic compounds is the 3-amino-1-(3,4-dichloro-2-methylbenzyl)-2-pyrazolin-5-one (muzolimine).

Suitable thiazolidones are especially 4-thiazolidones of formula VIII

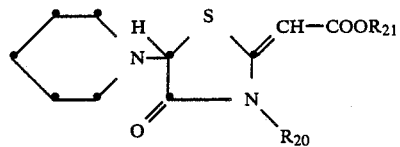

wherein R₂₀ and R₂₁ are hydrogen or lower alkyl of at most 4-C-atoms, such as methyl, ethyl, n-propyl, isopropyl and n-butyl.

Of particular interest are the following thiazolidones:
2-ethoxycarbonylmethylene-3-methyl-5-piperidino-4-thiazolidone (etozoline),
2-carboxymethylene-3-methyl-5-piperidino-4-thiazolidone (oxoziline), and
2-ethoxycarbonyl methylene-3-ethyl-5-piperidino-4-thiazolidone (piprozoline).

Imidazolidinones with diuretic properties are, for example, those of formula IX

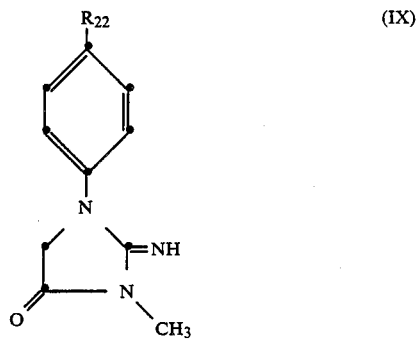

wherein R₂₂ is hydrogen or halogeno, especially chloro.

Of special interest in this group of compounds are:
2-imino-3-methyl-1-phenyl-4-imidazolidinone (azolimine), and 1-(p-chlorphenyl)-2-imino-3-methyl-4-imidazolidinone (calzolimine).

Particularly suitable cycloamidines are, for example, the 6-substituted 2,4,7-triamino-pteridines of formula X

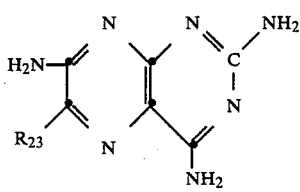

wherein R₂₃ is unsubstiututed phenyl or phenyl optionally substituted, e.g. by methyl, or methoxy, or furyl, e.g. 2-furyl.

Compounds of above formula X with particular interest are: 6-phenyl-2,4,7-triaminopteridine (triamterene), and 2,4,7-triamino-6-(2-furyl)-pteridine (furterene).

A further diuretic compound having cycloamidine-type structure, which is of major interest, is the N-amidino-3,5-diamino-6-chloropyrazinecarboxamide (amiloride).

Diuretic compounds having a spiroxane-type steroid structure are especially those of the formula

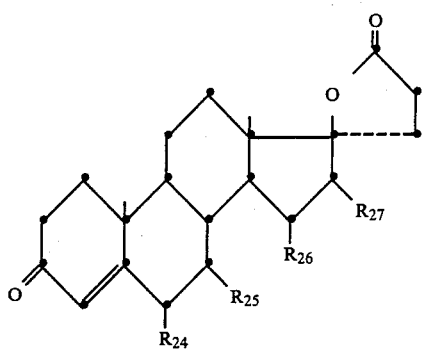

(XI)

in which $R_{24}$, $R_{26}$ and $R_{27}$ represent hydrogen and $R_{25}$, having the α-configuration, is acetylthio or lower alkoxycarbonyl, such as methoxycarbonyl or isopropyloxycarbonyl, or $R_{24}$ and $R_{25}$ together form an additional bond and $R_{26}$ and $R_{27}$ represent hydrogen, or $R_{24}$ and $R_{25}$ together form methylene and $R_{26}$ and $R_{27}$ each represents hydrogen or together form methylene.

Particularly mentioned as diuretic compounds having spiroxane-type steroid structures are:

7α-acetylthio-20-spirox-4-en-3,21-dione (spironolactone), 20-spiroxa-4,6-dien-3,21-dione (canrenone), 7α-methoxycarboxy-20-spirox-4-en-3,21-dione (mexrenone), 6β,7-methylene-20-spirox-4-en-3,21-dione (prorenone), and 6β,7; 15β,16-bis-methylene-20-spirox-4-en-3,21-dione (spirorenone).

Compounds of the above types having diuretic properties and being capable of forming salts, may be used in free form or in the form of pharmaceutically acceptable salts, those having basic properties in the form of corresponding acid addition salts, such as those with hydrochloric, sulfuric, phosphoric, acetic, lactic, maleic, fumaric, tartaric, citric, or methane sulphonic acid, those having acidic properties in the form of corresponding metal or ammonium salts, e.g. sodium, potassium, calcium, ammonium, diethylammonium or tri-(2-hydroxyethyl)-ammonium salts.

The magnesium supplementation can be used in the form of magnesium oxide, hydroxide or carbonate, but above all is used in the form of magnesium monoaspartate hydrochloride, which is usually available in the form of its trihydrate.

The potassium supplementation can be used in the form of a pharmaceutically acceptable inorganic or organic potassium salt, such as the potassium chloride or potassium citrate.

The active compounds used in the method of treating hypertension and/or congestive heart failure according to the present invention, i.e. the diuretic compound, the magnesium and optionally the potassium supplementation may be administered simultaneously or sequentially, e.g. with time intervals between the administation the different active compounds, whereby one or more than one type for each of the active compounds, particularly one or two compounds having diuretic effects, may be used.

Particularly preferred as compounds with diuretic properties are those of the group of thiazides and hydrothiazides, such as chlorothiazide and flumethiazide, and more particularly hydrochlorothiazide and bendroflumethiazide, as well as cyclothiazide, butizide, penflu- thiazide, hydroflumethiazide and methyclothiazide, those of the group of benzenesulfonamide, especially furosemide, chlorthalidone, bumetanide and indapamide, as well as oxomefruside, clofenamide, mefruside, clopamide and xipamide, those of the group of phenoxyacetic acids, particularly ethacrynic acid, as well as indacrinone, those of the cycloamidine group, particularly triamterene and amiloride, and those having a spiroxane-type steroid structure, such as spironolactone and canrenone, whereas the magnesium supplementation is primarily administered in the form of magnesium monoaspartate hydrochloride (usually as the trihydrate) and the optional potassium supplementation in the form of potassium chloride or potassium citrate.

Very particularly preferred as compounds with diuretic properties are bendroflumethiazide, hydrochlorothiazide, mefruside or chlorthalidone, whereas the magnesium supplementation is primarily administered in the form of magnesium monoaspartate hydrochloride (usually as the trihydrate) and the optional potassium supplementation in the form of potassium chloride.

The ratio of simultaneous or sequential administration of a diuretic compound, of magnesium and optionally potassium as supplementation as well as the new pharmaceutical preparation containing those active compounds can be varied within wide limits. The dosage depend on the activity of the particular diuretic compound and on the individual requirements of the patients.

The dosage of the diuretic compound selected from the groups consisting of the thiazides, thiadiazolesulfonamides, 6-substituted 2,4,7-triamino pteridines and the diuretic compounds having a spiroxane-type steroid structure may vary between 0.1–2.0 g/day, preferably between 0.2–1.0 g/day and the dosage of the diuretic compound selected from the group consisting of the hydrothiazides, benzenesulfonamides, phenoxyacetic acid derivatives, quinazolinesulfonamides, pyrazolinones, thiazolidones, imidazolidinones and of amiloride may vary between 1 to 200 mg/day, preferably between 2,0 to 50 mg/day and the dosage of the magnesium supplementation may vary between 50–800 mg/day of magnesium corresponding to 510–8100 mg of magnesium monoaspartate hydrochloride-trihydrate, 80–1320 mg of magnesium oxide, 120–1920 mg of magnesium hydroxide and 170–2780 mg of magnesium carbonate, (970–16,000 mg as magnesium hydroxide carbonate), preferably between 121.5–365 mg/day of magnesium corresponding to ca. 1230–3690 mg monoaspartate hydrochloride-trihydrate, 200–600 mg of magnesium oxide, 290–870 mg of magnesium hydroxide, and 425–1270 mg of magnesium carbonate (2425–7275 mg as magnesium hydroxide carbonate) and the dosage of optional potassium supplementation varies between 156–1560 mg/day of potassium corresponding to 300–3000 mg of potassium chloride and 1225–12,250 mg of potassium citrate, preferably between 312–780 mg/day of potassium corresponding to 600–1500 mg of potassium chloride and 2450–6125 mg of potassium citrate.

The sequential or simultaneous administration of above mentioned active agents, especially the administration of the pharmaceutical preparation according to the invention may be effected in a single dose or divided doses.

The active agents, such as diuretic compounds, magnesium and optionally the potassium supplementation may be administered simultaneously, together as a loose-grained mixture in a capsule or as a granulate in a bag (sachet) for mixing with water for drinking.

Further dosage forms for administration include tablets, syrups and suspended solutions. The active agents may be mixed with conventional inert pharmaceutical carriers and diluents.

EXAMPLE 1

A galenical form suitable for oral administration and comprising a diuretic compound and magnesium monoaspartate hydrochloride complex, corresponding to a magnesium content of 121.56 mg is given in table "A" below. The carriers are exemplary:

TABLE "A"

| | |
|---|---|
| Magnesium aspartate hydrochloride-trihydrate | 1242.9 mg |
| mefruside | 25.0 mg |
| sugar | 3202.1 mg |
| sacharine 75% | 10.0 mg |
| "mandarinearome Polyrome 3549" | 20.0 mg |
| citric acid | 500.0 mg |
| | 5000.0 mg | of a granulate to be filled in a sachet are obtained.

EXAMPLE 2

Preparation of 10,000 tablets each containing 614.5 mg magnesium mono-aspartate-hydrochloride trihydrate and 12.5 mg hydrochlorothiazide as active ingredient.

| Formula of the tablet: | |
|---|---|
| magnesium monoaspartatehydrochloride-trihydrate | 6145.0 g |
| hydrochlorothiazide | 125.0 g |
| calcium biphosphate | 700.0 g |
| cornstarch | 500.0 g |
| Aeorosil ® (collodial silicon dioxide) | 50.0 g |
| carboxymethylcellulose (sodium) | 200.0 g |
| talc | 50.0 g |
| magnesium stearate | 30.0 g |
| | 7800.0 g |

After granulating through a sieve, mixing and drying, the dried mixture is pressed to form 10,000 tablets, each weighing 780 mg. The tablets can, if desired, be provided with grooves for a more precise adjustment of the dosage amount.

EXAMPLE 3

A 61-year old woman who had suffered since her teens from relapsing urinary tract infections got the diagnosis of chronic pyelonephritis 20 years ago. In addition she has a fifteen year history of high blood pressure, left untreated the first five years. Thereafter she has received treatment with 12.5 mg/day hydrochlorothiazide and 600 mg/day potassium chloride supplementation. At the beginning of the study the woman's blood pressure was 145/90 mm Hg. After 2 months of 3690 mg/day magnesium monoaspartate hydrochloride-trihydrate in addition to her basic therapy her pressure was 125/85 mm Hg and after a reduction of magnesium momoaspartate-hydrochloride as trihydrate to 1230 mg/day her blood pressure after 6 months was 130/90.

EXAMPLE 4

A 62-year old woman with overweight has a twelve year history of high blood pressure. Initially her hypertension was treated with 2.5 mg/day bendroflumethiazide and 570 mg/day potassium chloride substitution. Later because of edema of the legs 40 mg of furosemide was added twice weekly instead of bendroflumethiazide. At the beginning of the study her blood pressure measures 160/100.

After 2 months of 3690 mg/day magnesium monoaspartate hydrochloride trihydrate in addition to her basic medicines her pressure was 150/95 and after 6 months 160/90.

EXAMPLE 5

A 57-year old woman was treated in her youth for tuberculosis. Until the onset of menopause she suffered from a long history of gynecological disorders resulting in three operations (including a right salpingo-oophorectomy) and in a period of prolonged treatment with oestrogen-gestagen contraceptives. Contraceptive therapy was finally terminated after the onset of serious side effects (including general edema and hypertension). The edema was first treated with 2 mg/day polythiazide, later replaced by 40 mg/day furosemide. Currently it is treated with 2.5 mg/day bendroflumethiazide and 570 mg/day potassium chloride supplementation. In recent years the woman also suffers from a nonspecific joint ailment for which she received piroxicam. At the beginning of the study her blood pressure measures 150/80 supine, 140/75 standing. After 4 1/2 months of 3690 mg of magnesium monoaspartate hydrochloride-trihydrate in addition to her basic medicines her pressure is 120/75 supine, 115/75 standing.

EXAMPLE 6

A 61year old essentially healthy woman has a ten year history of high blood pressure. Her hypertension was treated initially with 25 mg mefruside. At the beginning of the study her blood pressure was 160/100 mm Hg. After 6 months of treatment with 3690 mg of magnesium monoaspartate-hydrochloride-trihydrate in addition to her basic medicine of 25 mg of mefruside her blood pressure measured 150/85 mm Hg.

What is claimed is:

1. A method of treating hypertension or congestive heart failure in a patient in need thereof wherein the mean heart rate of said patient remains substantially unchanged comprising administering to said patient an antihypertensively effective amount of a diuretic compound selected from the group consisting of (a) a thiazide of formula I

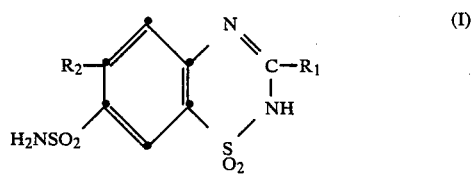

(b) a hydrothiazide of formula II

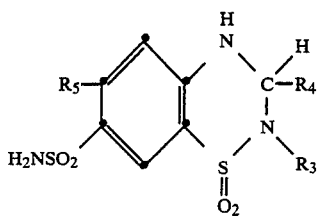

(c) a benzenesulfonamide of formula III

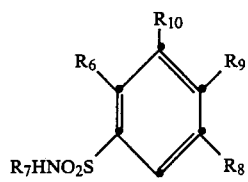

(d) a phenoxy acetic acid of formula IV

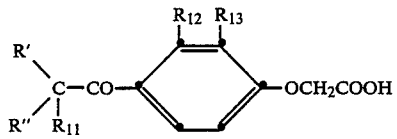

(e) a quinazolinesulfonamide of formula V

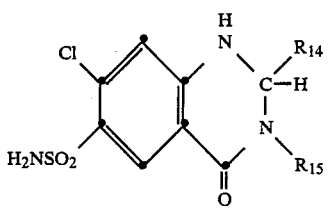

(f) a thiadiazolesulfonamide of formula VI

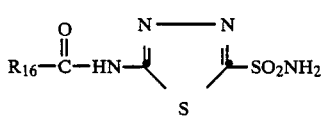

(g) a pyrazolinone of formula VII

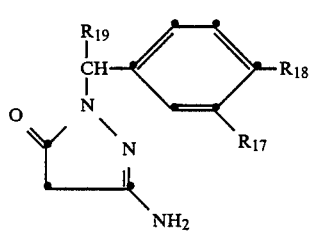

(h) a thiazolidone of formula VIII

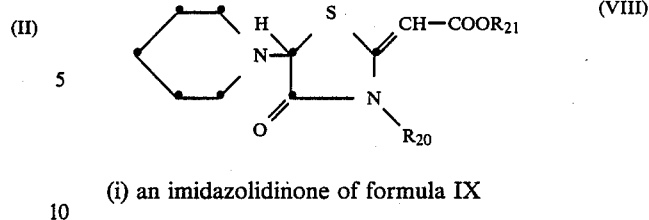

(i) an imidazolidinone of formula IX

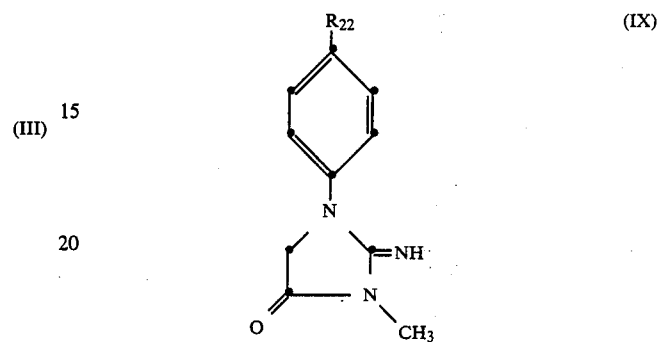

(j) a 6-substituted-2,4,7,-triamino-pteridine of formula X

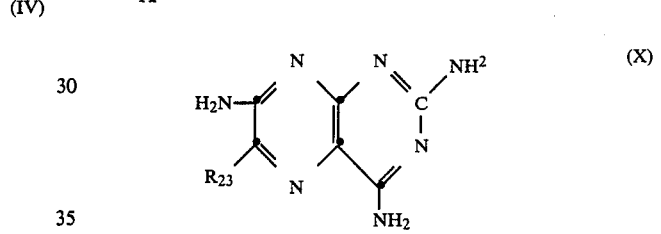

(k) N-amidino-3,5-diamino-6-chloro-pyrazine-carboramide, and (l) A spiroxane steroid compound of formula XI

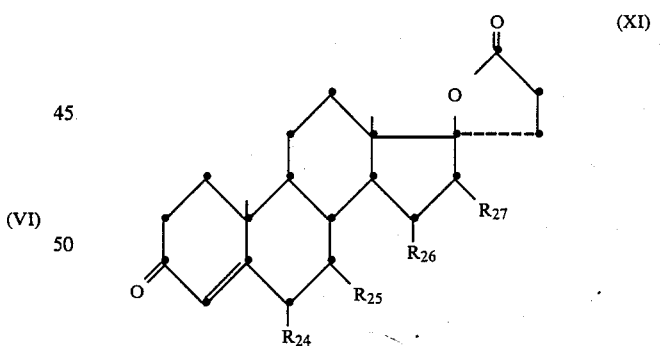

wherein $R_1$ is hydrogen or phenyl-lower alkylthio-lower alkyl;

$R_2$ is halogeno or trifluoromehtyl;

$R_3$ is hydrogen or methyl;

$R_4$ is hydrogen, $C_1$-$C_4$ alkyl, allyl, $C_5$-$C_8$ cycloalkyl or cycloalkenyl, $C_5$-$C_6$ cycloalkyl-lower alkyl, phenyl-lower alkyl, halophenyl-lower alkyl, halo-lower alkyl, lower alkylthio-lower alkyl, trifluoro-lower alkylthio-lower alkyl, lower alkenyl-thio-lower alkyl, phenyl-lower alkylthio-lower alkyl, or 2,5-dioxopyrrolidin-1-ylmethyl;

$R_5$ is halogen or trifluoromethyl;
$R_6$ is chloro;
$R_7$ is hydrogen;
$R_8$ is 3-hydroxy-1-oxo-isoindolin-3-yl;
$R_9$ is hydrogen;
$R_{10}$ is hydrogen;
$R'$ is lower alkyl;
$R''$ is phenyl;
or $R'$ and $R''$ together are methylene;
$R_{11}$ is lower alkyl or is methylene which is further bonded to the benzene ring of formula IV to yield an indanone ring;
$R_{12}$ is halogeno or lower alkyl;
$R_{13}$ is hydrogen, halogeno, or lower alkyl;
or $R_{12}$ and $R_{13}$ together represent but-1,3-dienylene-(1,4);
$R_{14}$ is lower alkyl or phenyl;
$R_{15}$ is hydrogen, phenyl, or o-tolyl;
$R_{16}$ is $C_1$–$C_4$ alkyl;
$R_{17}$ and $R_{18}$ are hydrogen or chloro;
$R_{19}$ is hydrogen or $C_1$–$C_4$ alkyl
$R_{20}$ and $R_{21}$ are independently hydrogen or $C_1$–$C_4$ alkyl;
$R_{22}$ is hydrogen or halogeno;
$R_{23}$ is phenyl which is unsubstituted or substituted by methyl, by methoxy, or by furyl;
$R_{24}$, $R_{26}$ and $R_{27}$ are hydrogen and $R_{25}$ is in the alpha-configuration and is acetylthio or lower alkoxycarbonyl; or $R_{24}$ and $R_{25}$ together form a bond and $R_{26}$ and $R_{27}$ each represent hydrogen; or $R_{24}$ and $R_{25}$ together are methylene and $R_{26}$ and $R_{27}$ are each hydrogen or together also are methylene; or a pharmaceutically acceptable salt thereof and
about 50 to about 800 mg of magnesium per daily dose of said composition in the form of magnesium monoaspartate hydrochloride.

2. The method of claim 1 wherein said diuretic compound is selected from the group consisting of compounds of formulae I-III, V-IX and XI, and N-amidino-3,5-diamino-6-chloro-pyrazine carboxamide.

3. The method of claim 1 wherein said diuretic compound is selected from the group consisting of
(a) thiazides and hydrothiazides consisting of chlorothiazide, flumethiazide, hydrochlorothiazide, bendroflumethiazide, clothiazide, butizide, penfluthiazide, hydroflumethiazide or methyclothiazide,
(b) benzenesulfonamides consisting of furosemide, mefruside, chlorthalidone, bumetanide, indapamide, oxomefruside, clofenamide, clopamide or xipamide,
(c) phenoxyacetic acids consisting of ethacrynic acid or indacrinone,
(d) cycloamidines consistng of triamterene or amiloride, and
(e) diuretic compounds having a spiroxane-type steroid structure consisting or spironolactone or canrenone.

4. The method of claim 3, wherein said diuretic is bendroflumethiazide, hydrochlorothiazide, mefruside or chlorthalidone, and said magnesium supplement is magnesium monoaspartate hydrochloride-trihydrate.

5. The method of claim 1 which comprises the simultaneous administration of said diuretic and said magnesium supplement.

6. The method of claim 1 which comprises the sequential administration of said diuretic, and said magnesium supplement.

7. The method of claim 1 which comprises the administration of one or two of said diuretic compounds and said magnesium supplement.

8. A method of treating hypertension or congestive heart failure in a patient in need thereof wherein the mean heart rate of said patient remains substantially unchanged comprising administering to said patient an antihypertensively effective amount of a diuretic compound selected from the group consisting of
(a) a thiazide of formula I

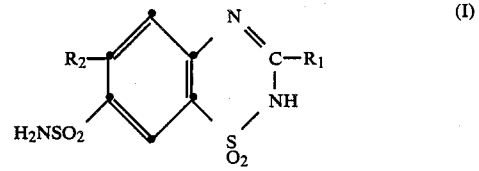

(b) a hydrothiazide of formula II

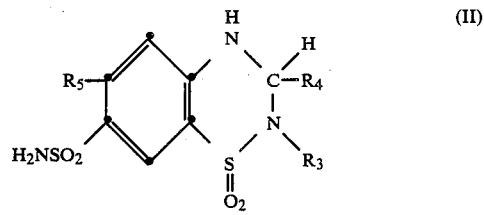

(c) a benzenesulfonamide of formula III

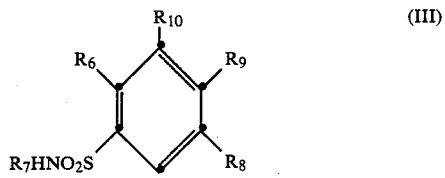

(d) a phenoxy acetic acid of formula IV

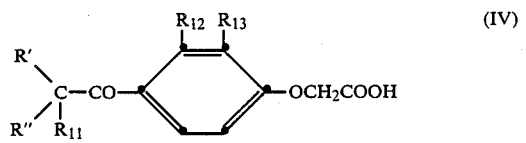

(e) a quinazolinesulfonamide of formula V

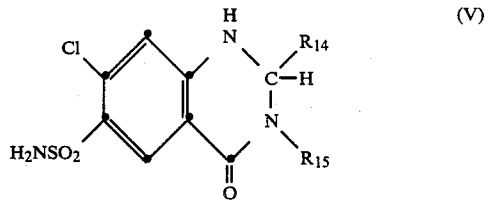

(f) a thiadiazolesulfonamide of formula VI

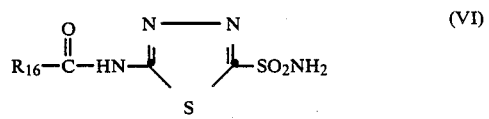

(g) a pyrazolinone of formula VII

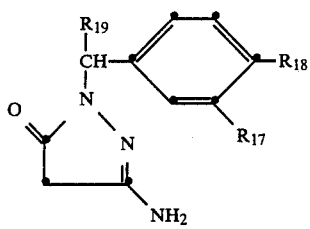
(VII)

(h) a thiazolidone of formula VIII

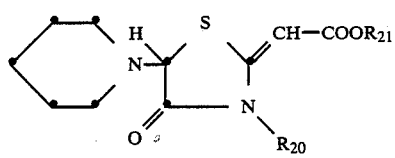
(VIII)

(i) an imidazolidinone of formula IX

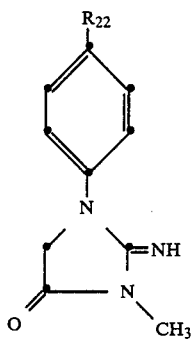
(IX)

(j) a 6-substituted-2,4,7-triamino-pteridine of formula X

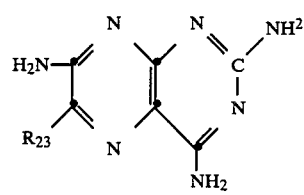
(X)

(k) N-amidino-3,5-diamino-6-chloro-pyrazine-carboramide, or (l) a spiroxane steroid compound of formula XI

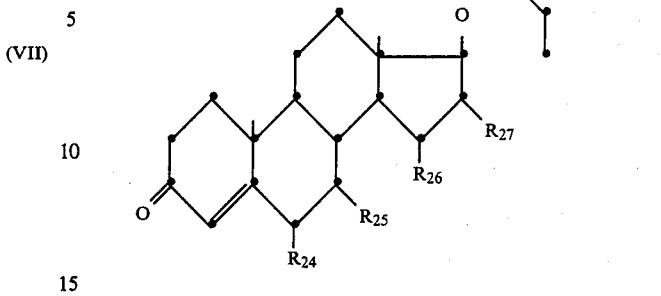
(XI)

wherein
$R_1$ is hydrogen or phenyl-lower alkylthio-lower alkyl;
$R_2$ is halogeno or trifluoromethyl;
$R_3$ is hydrogen or methyl;
$R_4$ is hydrogen, $C_1$–$C_4$ alkyl, allyl, $C_5$–$C_8$ cycloalkyl or cycloalkenyl, $C_5$–$C_6$ cycloalkyl-lower alkyl, phenyl-lower alkyl, halophenyl-lower alkyl, halo-lower alkyl, lower alkylthio-lower alkyl, trifluoro-lower alkylthio-lower alkyl, lower alkenylthio-lower alkyl, phenyl-lower alkylthio-lower alkyl, or 2,5-dioxopyrrolidin-1-yl-methyl;
$R_5$ is halogen or trifluoromethyl;
$R_6$ is chloro;
$R_7$ is hydrogen;
$R_8$ is 3-hydroxy-1-oxo-isoindolin-3-yl;
$R_9$ is hydrogen;
$R_{10}$ is hydrogen;
$R'$ is lower alkyl;
$R''$ is phenyl;
or $R'$ and $R''$ together are methylene;
$R_{11}$ is lower alkyl or is methylene which is further bonded to the benzene ring of formula IV to yield an indanone ring;
$R_{12}$ is halogeno or lower alkyl;
$R_{13}$ is hydrogen, halogeno, or lower alkyl;
or $R_{12}$ and $R_{13}$ together represent but-1,3-dienylene-(1,4);
$R_{14}$ is lower alkyl or phenyl;
$R_{15}$ is hydrogen, phenyl, or o-tolyl;
$R_{16}$ is $C_1$–$C_4$ alkyl;
$R_{17}$ and $R_{18}$ are hydrogen or chloro;
$R_{19}$ is hydrogen or $C_1$–$C_4$ alkyl
$R_{20}$ and $R_{21}$ are independently hydrogen or $C_1$–$C_4$ alkyl;
$R_{22}$ is hydrogen or halogeno;
$R_{23}$ is phenyl which is unsubstituted or substituted by methyl, by methoxy, or by furyl;
$R_{24}$, $R_{26}$ and $R_{27}$ are hydrogen and $R_{25}$ is in the alpha-configuration and is acetylthio or lower alkoxycarbonyl; or $R_{24}$ and $R_{25}$ together form a bond and $R_{26}$ and $R_{27}$ each represent hydrogen; or $R_{24}$ and $R_{25}$ together are methylene and $R_{26}$ and $R_{27}$ are each hydrogen or together also are methylene; or a pharmaceutically acceptable salt thereof and about 50 mg to about 800 mg per daily dose of said composition of magnesium in the form or magnesium monoaspartate hydrochloride; and about 156 to about 1560 mg per daily dose of said composition of potassium in the form of a pharmaceutically acceptable potassium salt.

9. The method of claim 8 wherein said diuretic compound is selected from the group consisting of compounds of formulae I–III, V–IX and XI, and N-amidino-3,5-diamino-6-chloro-pyrazine carboxamide.

* * * * *